(12) United States Patent
Duran Lopez

(10) Patent No.: US 7,375,231 B2
(45) Date of Patent: May 20, 2008

(54) INTERMEDIATE COMPOUND WHICH IS USED FOR THE PREPARATION OF PIOGLITAZONE

(75) Inventor: Ernesto Duran Lopez, Barcelona (ES)

(73) Assignee: Medichem S.A., Barcelona (ES)

( * ) Notice: Subject to any disclaimer, the term of this patent is extended or adjusted under 35 U.S.C. 154(b) by 0 days.

(21) Appl. No.: 10/555,659

(22) PCT Filed: May 4, 2004

(86) PCT No.: PCT/ES2004/070031

§ 371 (c)(1),
(2), (4) Date: Dec. 19, 2006

(87) PCT Pub. No.: WO2004/099147

PCT Pub. Date: Nov. 18, 2004

(65) Prior Publication Data

US 2007/0083050 A1    Apr. 12, 2007

(30) Foreign Application Priority Data

May 9, 2003    (ES) ............................... 200301075

(51) Int. Cl.
*C07D 417/00*    (2006.01)
*C07D 211/70*    (2006.01)
(52) U.S. Cl. .................................. 546/269.7; 546/335
(58) Field of Classification Search ............... 546/335, 546/269.7
See application file for complete search history.

(56) References Cited

U.S. PATENT DOCUMENTS 4,687,777 A    8/1987    Meguro et al.

FOREIGN PATENT DOCUMENTS

| JP | 8-325263 | 12/1996 |
| WO | WO 9638415 | * 12/1996 |
| WO | 02/088120 | 11/2002 |

OTHER PUBLICATIONS

West, Anthony R., Solid State Chemistry and its Applications, Wiley, New York, 1988, pp. 358 & 365.*
Patent Abstract of Japan of 2000-344748 dated Dec. 12, 2000.

* cited by examiner

*Primary Examiner*—Janet L. Andres
*Assistant Examiner*—Binta Robinson
(74) *Attorney, Agent, or Firm*—Ladas & Parry

(57) ABSTRACT

The present invention relates to a novel compound of formula (IV)

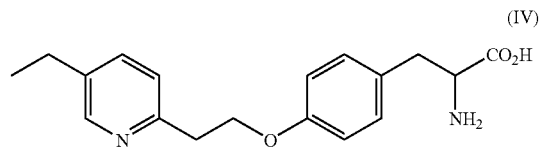

(IV)

which is an intermediate that can be used for the preparation of pioglitazone. It also relates to a method of obtaining the novel compound (IV) starting from the natural product L-tyrosine, in which the amino group is protected in the form of aromatic imino group, and a method of obtaining pioglitazone from the said intermediate.

10 Claims, No Drawings

INTERMEDIATE COMPOUND WHICH IS USED FOR THE PREPARATION OF PIOGLITAZONE

FIELD OF INDUSTRY

The present invention relates to an intermediate that can be used in the synthesis of pioglitazone, and its method of production starting from a natural product, L-tyrosine, and a method of obtaining pioglitazone from the said intermediate.

STATE OF THE PRIOR ART

Pioglitazone is the international common name of (±)-5-[[4-[2-(5-ethyl-2-pyridyl)ethoxy]phenyl]methyl]-2,4-thiazolidinedione of formula (I):

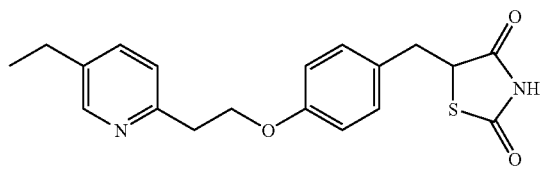

(I)

Pioglitazone and its antidiabetic properties were described for the first time in EP-A-193256.

The production of pioglitazone (I) from 2-(5-ethyl-2-pyridyl)ethanol and 4-fluoronitrobenzene is described in EP-A-193256. The main drawback of this process is the Meerwein reaction between the aniline derivative and methyl acrylate, catalysed by copper salts, which gives rise to by-products and takes place at low yields.

Methods are described in EP-A-257781, EP-A-506273 and EP-A-816340 for the production of pioglitazone that include the reaction of a derivative of 2-(5-ethyl-2-pyridyl)ethanol, in which the hydroxyl group is activated by a leaving group, with an alkali metal salt of p-hydroxybenzaldehyde. The said production process includes a stage of hydrogenation at high pressure that is difficult to scale up industrially since special plants are required. Patent application WO9313095A1 attempted to solve this problem by using sodium borohydride as reducing agent and cobalt chloride, which is highly toxic, as catalyst.

Two methods that can use tyrosine, a natural amino acid, as the starting product for the production of pioglitazone are disclosed in patent application WO02088120A1.

One of the said methods is described in example 3 of patent application WO02088120A1. The overall yield of the said process is less than 10%, which proves to be too low for the process to be regarded as industrially useful.

The other method of patent application WO02088120A1 that also uses tyrosine as starting product is only disclosed in a general manner, and the cited patent application does not contain any concrete description of a practical realization thereof. The said method disclosed in a general way includes the reaction of the natural amino acid L-tyrosine (II)

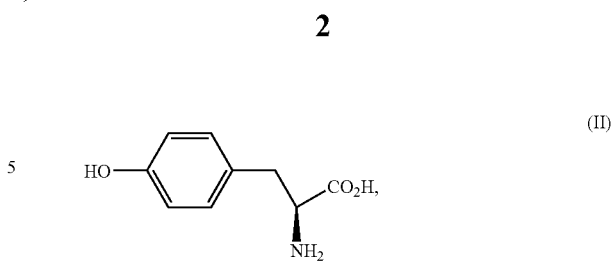

(II)

or an ester thereof, with a compound of formula (III)

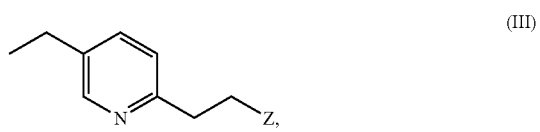

(III)

in which Z is a leaving group, for the supposed production of the compound of formula (IV)

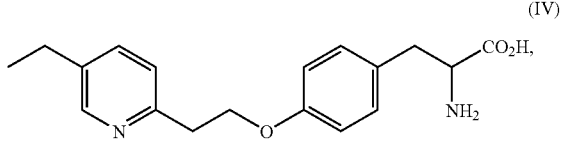

(IV)

which, after several additional stages, would lead to pioglitazone. The cited patent application does not describe compound (IV), or a method for its preparation.

However, direct reaction between L-tyrosine or an ester thereof with the compound of formula (III) proves unworkable in practice. The authors of the present invention have demonstrated experimentally that the said reaction gives rise to the unwanted compound (V)

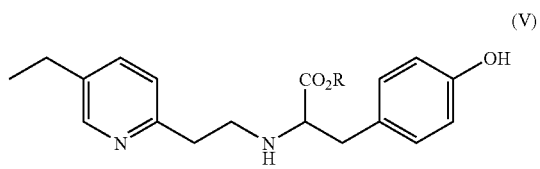

(V)

This compound (V) is produced by a reaction of N-alkylation of the amino group of L-tyrosine on compound (III) with elimination of the leaving group Z. The compound (V) obtained is not an intermediate whose structure makes it possible to obtain pioglitazone, in accordance with the synthetic scheme proposed in patent application WO02088120A1.

There is thus a need for a method of production of pioglitazone starting from a product that is easily accessible as is natural L-tyrosine at a good yield.

Patent application JP-A-2000344748 describes the methyl ester of formula (VI)

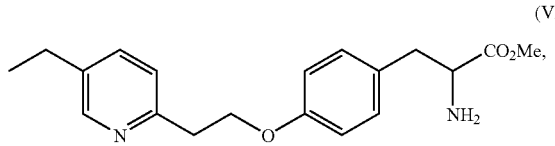

which is used in the production of compounds with a structure that is clearly different from pioglitazone, as they do not possess the structure derived from thiourea that is present in pioglitazone.

OBJECT OF THE INVENTION

The object of the invention is a novel intermediate that can be used in the preparation of pioglitazone.

In a second aspect, another object of the invention is a method of production of the novel intermediate.

In a third aspect, another object of the invention is a method based on the preceding method that includes, moreover, additional stages that make it possible to obtain pioglitazone.

In a fourth aspect, another object of the invention is the use of the novel intermediate in the preparation of pioglitazone.

DETAILED DESCRIPTION OF THE INVENTION

The present inventors have discovered a novel compound that is an intermediate that can be used in the preparation of pioglitazone. This compound, not described previously, can be obtained by a simple method starting from a raw material of natural origin, and easily accessible, as is the amino acid L-tyrosine. Furthermore, the said intermediate can be converted to pioglitazone at a good yield.

The novel compound corresponds to formula (IV):

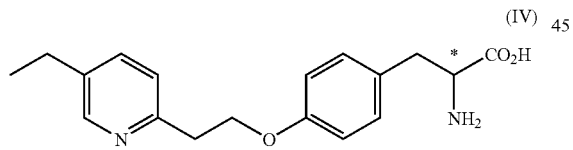

The compound of formula (IV) has a chiral centre, marked with an asterisk in the above formula, therefore it can be in the form of either one of its two pure enantiomers, of racemic mixtures, or of mixtures enriched in either one of its two enantiomers. All these forms that have been mentioned are included in the present invention. Compound (IV) can also be in the form of salts, solvates and hydrates.

The object of the second aspect of the invention is a method of production of compound (IV).

Preparation of the compound of formula (IV) from L-tyrosine or an ester thereof requires the reaction of L-tyrosine with compound (III) to take place via the phenolic hydroxyl group of L-tyrosine, and not via the amino group thereof. As mentioned previously with regard to patent application WO02088120A1, direct reaction between the two compounds leads to the unwanted intermediate of formula (V).

It might be thought a priori that a solution to the problem might consist of protecting the amino group in L-tyrosine, to avoid the unwanted reaction of the said amino group with the electrophilic group Z of compound (III), and in this way obtain the correct intermediate of formula (IV).

However, the present inventors found that protection of the amino group of L-tyrosine, or of an ester thereof, by means of the usual protecting groups of amino groups such as acetyl, tert-butyloxycarbonyl, benzyloxycarbonyl or ethyloxycarbonyl, does not solve the problem, since use of the said protecting groups only makes it possible to obtain compound (IV) at a very low yield.

The inventors discovered that, surprisingly, protection of the amino group of L-tyrosine or of an ester thereof in the form of aromatic imino group solves the stated problem, making it possible to prepare compound (IV) at high yield without giving rise to unwanted intermediates, which in its turn makes it possible to obtain pioglitazone (I) at good yields and in good conditions of purity.

Thus, the compound of formula (IV) can be prepared at good yields according to a method that comprises reaction of a compound of formula (VII)

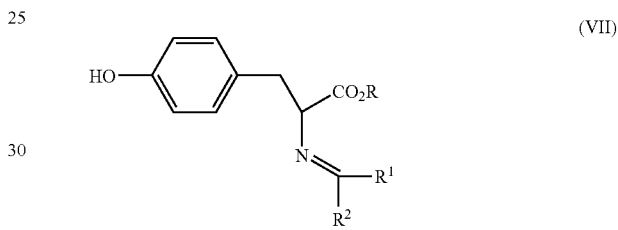

in which: R can be hydrogen or a $C_1$-$C_4$ alkyl group;
$R^1$ and $R^2$ can be, without distinction, hydrogen or an aryl group of formula

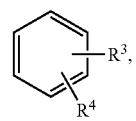

in which $R^3$ and $R^4$ can be, without distinction, hydrogen, or a $C_1$-$C_6$ alkyl group, or a $C_1$-$C_4$ alkoxy group;
with the condition that $R^1$ and $R^2$ cannot both be hydrogen, with a compound of formula (III)

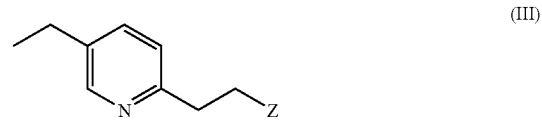

in which Z is a leaving group, to obtain the compound of formula (VIII)

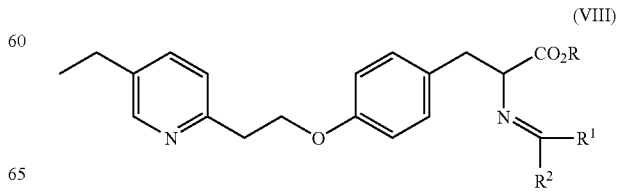

which, subsequently, is submitted to deprotection of the amino group and hydrolysis of the ester group.

The compound of formula (VII), in which the amino group is protected in the form of an aromatic imino group, can be obtained from L-tyrosine or from an ester thereof of formula (IX)

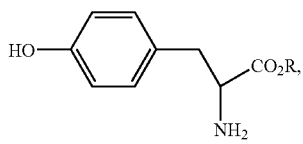

in which R has the meaning stated previously, by reaction with a carbonyl compound of formula

R¹COR², in which R¹ and R² have the meanings stated previously.

These reactions of protection of the amino group can be carried out according to any one of the methods described in the book "Protective Groups in Organic Synthesis" by T. W. Greene and P. G. M. Wuts, Third Edition, Publishers John Wiley & Sons, 1999 (ISBN 0-471-16019-9) (pages 586-589). For example, the reaction of an amino group with benzaldehyde (R¹=hydrogen and R²=phenyl) protects the said amino group in the form of benzylideneamino.

Preferably R is selected from hydrogen, methyl, ethyl, propyl, isopropyl, n-butyl, sec-butyl or tert-butyl. More preferably, R is the methyl group.

Preferably R¹ is hydrogen and R² is an aryl group

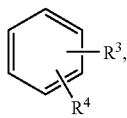

in which $R^3$ and $R^4$ can be, without distinction, hydrogen, a $C_1$-$C_6$ alkyl group, or a $C_1$-$C_4$ alkoxy group, and more preferably R¹ is hydrogen and R² is phenyl.

The compound of formula (IX), in the case when R is a $C_1$-$C_4$ alkyl group, is an ester of tyrosine, which can be obtained by esterification of L-tyrosine (II) with a $C_1$-$C_4$ aliphatic alcohol, using acid catalysis. Optionally the carboxyl group of L-tyrosine can be activated to facilitate reaction with the $C_1$-$C_4$ aliphatic alcohol.

The compound of formula (IX) in which the group R is a methyl group, i.e. the methyl ester of tyrosine, is especially preferred. This compound can be obtained by reaction of L-tyrosine (II) with methanol in the presence of thionyl chloride, as activating agent of the carboxyl group of L-tyrosine.

The compounds of formula (III)

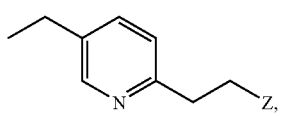

in which Z is a leaving group, can be obtained by conventional methods. For example, the compound in which the leaving group Z is a methanesulphonic ester (mesylate) can be obtained according to the method described in the example of reference 2 of EP-A-506273, cited previously, from 2-(5-ethylpyridin-2-yl)ethanol, (X):

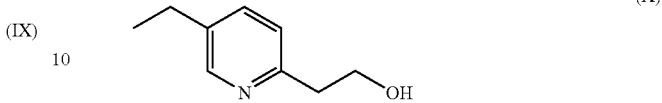

The group Z present in the compounds of formula (III) is a leaving group that is liable to nucleophilic attack. Leaving groups are known by a person skilled in the art and are described in the book "Advanced Organic Chemistry" by J. March, 3rd Edition, published by John Wiley & Sons, 1985 (pages 310-316). As an example, and non-exhaustively, the leaving groups can be:

Halogen atoms (fluorine, chlorine, bromine, iodine)

Sulphonic esters (tosylate, brosylate, nosylate, mesylate)

Fluoroalkylsulphonic esters (triflates, nonaflates, tresylates)

Oxonium ions

Alkyl perchlorates

Esters of ammonioalkanesulphonates (betylates)

Groups Z in which the leaving group is a sulphonic ester, more preferably the methanesulphonyl group (mesyl=OMs), are preferred.

The reactions of deprotection of the amino protecting group are known by a person skilled in the art and are described in the book by T. W. Greene et al., cited previously. In the case of the benzylideneamino group, deprotection can be effected, for example, by treatment with hydrochloric acid, or by hydrogenation catalysed by palladium on carbon as catalyst, or by reaction with hydrazine under ethanol reflux.

The reaction of hydrolysis of the ester group is well known by a person skilled in the art and can be carried out both in acid medium and in alkaline medium.

The inventors demonstrated experimentally that the racemization occurs in the process that has been developed and product (IV) is obtained in racemic form. This makes it possible to use, as starting product, the enantiomerically pure and more economical form of the natural amino acid tyrosine (L-tyrosine), and it is not necessary to use the more expensive racemic tyrosine, for obtaining the pioglitazone, which is also marketed in racemic form.

In a preferred embodiment of the invention, the compound of formula (IV)

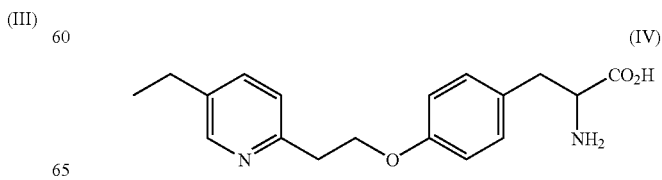

is obtained by a method that comprises reaction of the compound of formula

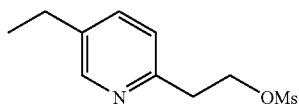

with the compound of formula

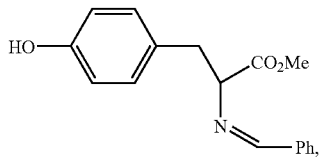

to obtain the compound of formula

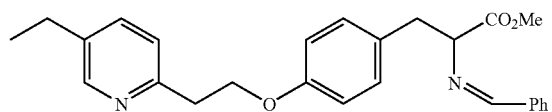

which is submitted subsequently to deprotection of the benzylideneamino group and hydrolysis of the methyl ester.

In a third aspect of the invention, the method of production of compound (IV) further comprises the following stages for obtaining pioglitazone (I):

(a) bromination of compound (IV) to obtain the compound of formula (XI)

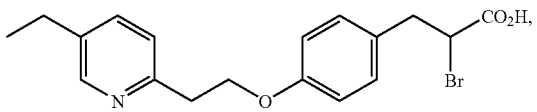

(b) condensation of compound (XI) with thiourea to obtain the compound of formula (XII)

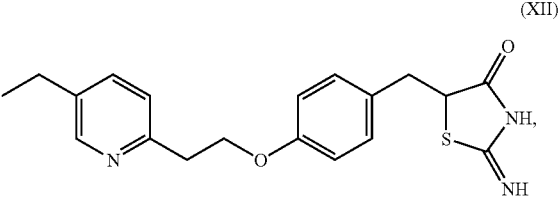

(c) hydrolysis of compound (XII) to obtain pioglitazone.

Stage (a) of bromination of compound (IV) can be carried out according to any of the methods described in WO002088120A1, cited previously, for analogous compounds. For example, by diazotization with sodium nitrite of the amino group of compound (IV) dissolved in aqueous hydrobromic acid.

In stage (b), reaction of compound (XI) with thiourea can be carried out, for example, according to the method described in example 3 of WO002088120A1 for an analogous compound. Thus, compound (XI) reacts with thiourea in ethanol medium at the reflux temperature in the presence of sodium acetate, to give compound (XII).

It will be obvious, to a person skilled in the art, that stage (b) can also be carried out in an equivalent manner between thiourea and a $C_1$-$C_4$ alkyl ester of compound (XI).

Stage (c) consists of hydrolysis of compound (XII) to obtain pioglitazone, and can be carried out according to example 1 section d) of EP-A-193256, cited previously. In the said example, compound (XII) is treated with aqueous hydrochloric acid at the reflux temperature and, after a conventional process of isolation, crystals of pioglitazone are obtained.

EXAMPLES

Example 1

Production of compound (IV)

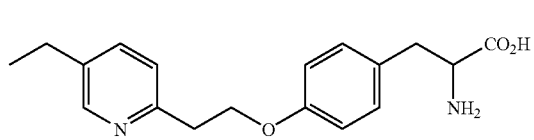

1.A.—Production of compound (VII), in which R=methyl, $R^1$=hydrogen and $R^2$=phenyl

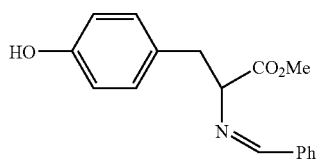

Place 5.10 g (28.1 mmol) of L-tyrosine in a 100-mL three-necked flask fitted with a magnetic stirrer, and suspend in 30 mL of methanol. Cool the suspension to 0° C. on a water/ice bath. Add 4.5 mL (62.0 mmol) of thionyl chloride in 20 minutes. On completion of addition, remove the ice bath and leave to warm to room temperature. Next, heat the suspension under reflux for 4.5 h. Leave to cool, and evaporate the solvent to dryness in the rotary evaporator. A solid is obtained, the methyl ester of tyrosine, at practically quantitative yield.

82.9 g (425 mmol) of the solid obtained in the preceding stage and 43.2 mL (425 mmol) of benzaldehyde were added to 1.1 L of dichloromethane at room temperature. The resulting suspension was stirred at room temperature overnight. Next, the solvent was evaporated at reduced pressure, to obtain the methyl ester of tyrosine with the amino group protected in the form of benzylideneamino, compound (VII) in which R=methyl, $R^1$=hydrogen and $R^2$=phenyl, in the form of oil, which is used in stage 1.B.

1.B.—Production of compound (IV)

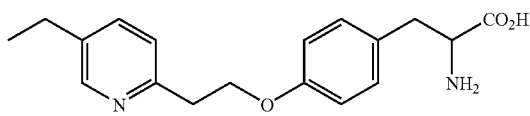

66.0 g (436 mmol) of 2-(5-ethylpyridin-2-yl)ethanol was dissolved in 500 mL of toluene. 72.5 mL (523 mmol) of triethylamine was added to this solution, at room temperature. The resulting solution was cooled between 0 and 10° C., after which 34.0 mL (438 mmol) of methanesulphonyl chloride was added dropwise during 75 minutes. When addition was completed, it was stirred for 1 hour at room temperature. Next, the organic phase was washed with a saturated solution of sodium bicarbonate (400 mL) and with water (400 mL), and was dried over sodium sulphate, obtaining a toluene solution of 2-(5-ethylpyridin-2-yl)ethyl methanesulphonate, a compound of formula (III) in which Z=OMs.

The said solution in toluene (equivalent to 436 mmol) was added to a mixture containing 120 g (425 mmol) of the compound obtained in stage 1.A, 64.5 g (467 mmol) of potassium carbonate and 2.7 g (8.4 mmol) of tetrabutylammonium bromide. An additional 700 mL of toluene was added, and the resulting suspension was stirred at 70° C. After 8 hours, a further 110 mL of the aforementioned solution in toluene (equivalent to 93 mmol) and 14.0 g (191 mmol) of potassium carbonate were added to the reaction mixture, stirring of which continued at 70° C. After 30 hours, 2.7 g (8.4 mmol) of tetrabutylammonium bromide was added. Once reaction was completed (40 hours), the suspension obtained was used directly, without purification, in the next stage.

1360 mL of 2N HCl was added to the suspension obtained in the preceding stage. The resulting mixture was stirred for 1 hour at 70° C. The phases were decanted and the aqueous phase was extracted, discarding the toluene phase. The aqueous phase was returned to the reactor and was alkalized by addition of aqueous solution of NaOH at 50%. After alkalization, the resulting solution was stirred for 2 hours at 70° C. After cooling, the aqueous phase was washed with toluene (2×250 mL) and was neutralized with concentrated HCl to pH 5, with precipitation of a solid of a pale yellow colour that was filtered in a Buchner funnel.

The filtered solid was digested in 825 mL of water and was recrystallized from methanol, obtaining (±)-2-amino-3-[4-[2-(5-ethylpyridin-2-yl)ethoxy]phenyl]propionic acid, compound (IV) (83.9 g, 62.8% overall yield from L-tyrosine) in the form of a solid of a pale yellow colour. It was demonstrated by chiral HPLC and by experiments of optical rotatory dispersion that the product is obtained in the form of a racemic mixture.

The compound is very slightly soluble in the usual solvents for NMR. To record its 1H and 13C spectra, an aliquot in 1M HCl is dissolved in MeOH (anhydrous), followed by solvent evaporation at reduced pressure. Consequently, the NMR spectra recorded correspond to the double hydrochloride of compound (IV). The spectral data are as follows:

$^1$N-NMR (CD$_3$OD, 400 MHz) δ (ppm): 8.68 (s, 1 H, H6 pyridine), 8.48 (d, $^3J_{H3\text{-}H4}$=7.8 Hz, 1 H, H4 pyridine), 8.05 (d, $^3J_{H3\text{-}H4}$=7.8 Hz, 1 H, H$_3$ pyridine), 7.22 (d, $^3J_{H2\text{-}H3}$=8.6 Hz, 2 H, H3 benzene), 6.93 (d, $^3J_{H2\text{-}H3}$=8.6 Hz, 2 H, H2 benzene), 4.42 (t, $^3J_{H\text{-}H}$=5.6 Hz, 2 H, pyr-CH$_2$—CH$_2$O—), 4.21 (dd, $^3J_{Hb\text{-}H}$=7.2 Hz, $^3J_{Ha\text{-}H}$=6.0 Hz, 1 H, —CH—COOH), 3.54 (t, $^3J_{H\text{-}H}$=5.6 Hz, 2 H, pyr-CH$_2$—CH$_2$O—), 3.23 (dd, $^2J_{Ha\text{-}Hb}$=14.4 Hz, $^3J_{Ha\text{-}H}$=6.0 Hz, 1 H, H$_a$ benzyl), 3.13 (dd, $^2J_{Ha\text{-}Hb}$=14.4 Hz, $^3J_{Hb\text{-}H}$=7.2 Hz, 1 H, H$_b$ benzyl), 2.89 (q, $^3J_{H\text{-}H}$=7.4 Hz, 2 H, pyr-CH$_2$—CH$_3$), 1.33 (t, $^3J_{H\text{-}H}$=7.4 Hz, 3H, pyr-CH$_2$—CH$_3$). $^{13}$C-NMR (CD$_3$OD, 100 MHz) δ (ppm): 171.11 (—COOH), 159.18 (C2 pyridine), 153.15 (C1 benzene), 147.73 (C4 pyridine), 143.83 (C5 pyridine), 140.95 (C6 pyridine), 131.76 (C3 benzene), 128.82 (C3 pyridine), 128.19 (C4 benzene), 116.17 (C2 benzene), 66.89 (pyr-CH$_2$—CH$_2$O—), 55.16 (—CH—COOH), 36.36 (CH$_2$ benzyl), 34.15 (pyr-CH$_2$—CH$_2$O—), 26.30 (pyr-CH$_2$—CH$_3$), 14.85 (pyr-CH$_2$—CH$_3$).

Example 2

Production of Pioglitazone (I)

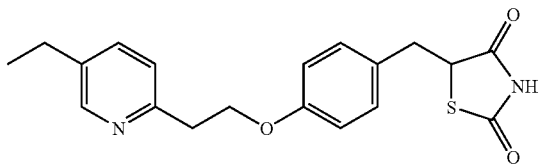

60.0 g (190.9 mmol) of compound (IV) is placed in a 500-mL three-necked flask and is suspended in 170 mL of water. 86.0 mL (765.2 mmol) of concentrated hydrobromic acid (48%) is added, observing dissolution of the starting compound. The resulting solution is cooled on a water/ice bath to 3° C. 20.4 g (295.7 mmol) of sodium nitrite dissolved in 41 mL of water is added slowly (1 h), via a pressure-equalizing dropping funnel. On completion of addition, it is stirred for 3 hours on the water/ice bath and at room temperature over night. On the next day, precipitation of a brown coloured oil is observed, which is extracted with dichloromethane. After drying and evaporating the organic phase, a reddish oil is obtained, which is used directly in the next stage.

The oil obtained in the preceding stage is introduced, together with 25.0 g (328.4 mmol) of thiourea and 28.0 g (341.3 mmol) of anhydrous sodium acetate, into a single-necked 1 L flask equipped with a magnetic stirrer. The mixture is suspended in 585 mL of absolute ethanol, and is stirred under reflux for 5 hours. It is left, with stirring at room temperature, over night. The solvent is evaporated to dryness in the rotary evaporator, and the residue obtained is suspended in a mixture of 175 mL of saturated sodium bicarbonate solution and 175 mL of ethyl acetate. The resulting suspension is stirred for 3 hours at room temperature, and the precipitated solid is filtered in a Buchner funnel, washing it with 2×85 mL of ethyl acetate. 34.4 g of a reddish solid is obtained which is identical on the basis of NMR and HPLC to a sample of compound (XII) synthesized by the route described in patent EP193256B1.

29.9 g (84.1 mmol) of the reddish solid obtained in the preceding stage is introduced into a 1 L three-necked flask equipped with a mechanical stirrer. 240 mL of water and 36.8 mL of concentrated hydrochloric acid are added, and the resulting solution is stirred for 8 hours under reflux. The mixture obtained is neutralized with NaOH to pH 8 and the solid obtained is filtered. 23.6 g (yield of 40.7% from product (IV) of pioglitazone is obtained.

The overall yield from L-tyrosine to pioglitazone is 25.6%.

Comparative Example 1

Production of Compound (IV) Using the Tert-butyloxycarbonylamino Group as the Amino Protecting Group A 250-mL flask, equipped with a magnetic stirrer and under anhydrous atmosphere, is loaded with 10.0 g (51.4 mmol) of methyl ester of L-tyrosine, which is then dissolved in 50 mL of dichloromethane. 14.2 mL (102.4 mmol) of triethylamine is added and the solution is cooled to 0° C. with a water/ice bath. A solution of 13.4 g (61.4 mmol) of di-tert-butyl bicarbonate ($Boc_2O$) in 30 mL of dichloromethane is added slowly (2.5 h). At the end of addition, it is left over night, with stirring at room temperature. 100 mL of water is added and the organic phase is extracted, and washed with 2×20 mL of water, 2×40 mL of 1M HCl, 2×40 mL of water and 2×40 mL of saturated NaCl solution. The organic phase is dried and evaporated, obtaining 13.7 g (90.4% yield) of an oil, which is used in the subsequent substitution reaction.

A 500-mL three-necked flask, equipped with a mechanical stirrer, is loaded with the 13.7 g (46.4 mmol) of the oil obtained in the preceding stage, 10.6 g (46.2 mmol) of 2-(5-ethylpyridin-2-yl)ethyl methanesulphonate, obtained by evaporation of the solution in toluene resulting from the first stage of example 1.B, and 7.0 g (50.6 mmol) of potassium carbonate. 150 mL of toluene and 50 mL of MeOH are added, and the mixture is stirred under reflux (65° C.) for 18 hours. After this time, the solvent is evaporated and the residue obtained is redissolved in 50 mL of AcOEt and 20 mL of water. The organic phase is extracted and washed with 2×20 mL of 10% NaOH. It is dried and the organic phase is evaporated to dryness. An oil is obtained that weighs 14.6 g, and this is submitted without purification to the stage of deprotection of the tert-butyloxycarbonylamino group.

The 14.6 g (34.0 mmol) of the oil obtained in the preceding stage is placed in a 250-mL flask equipped with a magnetic stirrer. 10.1 g (179.5 mmol) of KOH is added, and the mixture is dissolved in 100 mL of methanol/water 1:1. The resulting solution is heated under reflux for 2 hours. The methanol is evaporated in the rotary evaporator and the aqueous phase is extracted with 2×30 mL of ethyl acetate. The organic phase is dried and evaporated. An oil weighing 15.9 g is obtained. The said oil is placed in a 250-mL flask and is dissolved in 200 mL of MeOH. 9.2 mL (126.1 mmol) of thionyl chloride is added, and the solution is heated under reflux for 1 hour. The solvent is evaporated in the rotary evaporator. The raw product obtained is redissolved in 50 mL of dichloromethane. Saturated sodium bicarbonate solution is added until pH 6 is reached. The organic phase is extracted, dried and evaporated to dryness. 6.43 g (42.3% overall yield for the stages of substitution and deprotection) of an oil is obtained and is submitted directly to the stage of hydrolysis of the methyl ester.

3.47 g (10.6 mmol) of the oil obtained in the preceding stage is placed in a 250-mL flask equipped with a magnetic stirrer, and is dissolved in a mixture of 40 mL water and 40 mL methanol. 1.2 g (21.4 mmol) of KOH is added and the mixture is heated under reflux for 1 hour. On cooling, a yellowish solid begins to precipitate. The methanol is evaporated in the rotary evaporator. The resulting aqueous solution is neutralized to pH 5. The solid obtained is filtered and then dried in a vacuum stove. 2.09 g (63.0% yield) of compound (IV) is obtained.

The overall yield from the methyl ester of L-tyrosine to compound (IV) using the tert-butyloxycarbonylamino protecting group is only 24.1%.

Comparative Example 2

Production of Compound (IV) Using the Benzyloxycarbonylamino Group as the Amino Protecting Group 28.4 g (122.6 mmol) of tyrosine methyl hydrochloride and 54.2 g (782.8 mmol) of potassium carbonate are placed in a 1 L three-necked flask equipped with a mechanical stirrer. The solids are dissolved in a mixture of 160 mL water and 160 mL acetone. A clear solution is obtained, which is cooled to 5° C. on a water/ice bath. 27.5 mL (195.4 mmol) of benzyl chloroformate is added, in 30 minutes, via a pressure-equalizing dropping funnel. At the end of addition, the resulting yellowish suspension is stirred over night at room temperature. At the end of this time, 100 mL of ethyl acetate is added, the mixture is transferred to a decanting funnel and the organic phase is separated, which is dried and evaporated to dryness. 44.3 g (92.2% yield) of an oil is obtained, which is used in the next reaction of substitution.

A 1 L three-necked flask equipped with a magnetic stirrer is loaded with the 44.3 g (134.6 mmol) of oil obtained in the preceding stage, 37.3 g (162.5 mmol) of 2-(5-ethylpyridin-2-yl)ethyl methanesulphonate, obtained by evaporation of the solution in toluene resulting from the first stage of example 1.B, and 22.3 g (161.3 mmol) of potassium carbonate. The mixture is suspended in 500 mL of isopropyl acetate, and is heated under reflux for 96 hours. After 20 hours, 0.87 g (2.7 mmol) of tetrabutylammonium bromide is added. After leaving to cool to room temperature, the suspension obtained is transferred to a decanting funnel and is washed with 2×200 mL of 10% NaOH. The organic phase is dried and evaporated. 39.5 g of an oil is obtained, which is used without purification in the next reaction of deprotection.

The oil obtained in the preceding stage is placed in a 2 L single-necked flask equipped with a magnetic stirrer, and is dissolved in 100 mL of methanol. 100 mL of 10% NaOH is added, and the mixture is heated under reflux for 3 hours. Then 100 mL of concentrated hydrochloric acid (37%) is added and it is heated under reflux for 18 hours. At the end of this time, it is left to cool to room temperature and the methanol is evaporated in the rotary evaporator. The aqueous phase is washed with 100 mL of toluene. It is neutralized to pH 5 by adding 50% NaOH solution, observing the precipitation of a white solid, which is filtered in a Buchner funnel. 2.43 g (22.4% overall yield in the stages of substitution and deprotection) of compound (IV) is obtained.

The overall yield from the methyl ester of L-tyrosine to compound (IV) using the benzyloxycarbonylamino protecting group is only 20.7%.

Comparative example 3

Production of Compound (IV) Using the Acetylamino Group as the Amino Protecting Group A 500-mL three-necked flask equipped with a mechanical stirrer is loaded with 15.1 g (77.3 mmol) of methyl ester of L-tyrosine and 9.0 g (84.9 mmol) of sodium carbonate. The solids are suspended in a mixture of 200 mL dichloromethane and 60 mL water. With vigorous mechanical stirring, 6.9 mL (97.0 mmol) of acetyl chloride is added via a pressure-equalizing dropping funnel. The suspension is stirred for 30 minutes at room temperature and for a further 30 minutes under dichloromethane reflux. Dissolution of a high proportion of the suspended solid is observed, and it precipitates again on cooling. 2×50 mL of ethyl acetate is added, which dissolves the precipitated solid, and the organic phase is extracted, which is dried and evaporated to dryness. 15.6 g (85.0% yield) of a solid is obtained, which is used directly in the next reaction.

A 250-mL three-necked flask, equipped with a mechanical stirrer, is loaded with 5.03 g (21.2 mmol) of the solid obtained in the preceding stage, 4.85 g (21.2 mmol) of 2-(5-ethylpyridin-2-yl)ethyl methanesulphonate, obtained by evaporation of the solution in toluene resulting from the first stage of example 1.B, 2.92 g (21.1 mmol) of potassium carbonate and 0.15 g (0.47 mmol) of tetrabutylammonium bromide. The mixture is suspended in 50 mL of toluene, and is stirred under reflux for 16 hours. The resulting suspension is used directly in the next stage.

The suspension obtained in the preceding stage is placed in a 250-mL three-necked flask equipped with a mechanical stirrer, and 100 mL of 10% NaOH is added. It is heated under reflux for 7 hours. At the end of this time, the resulting mixture is transferred to a decanting funnel and the aqueous phase is extracted. It is neutralized with concentrated HCl to pH 5, precipitating a beige-coloured solid which is filtered in a Buchner funnel and is dried in a vacuum stove. 0.90 g (14% overall yield of substitution and deprotection) of compound (IV) is obtained.

The overall yield from the methyl ester of L-tyrosine to compound (IV) using the acetylamino protecting group is only 11.5%.

Comparative Example 4

Production of Compound (IV) Using the Ethyloxycarbonylamino Group as the Amino Protecting Group 10.1 g (51.7 mmol) of methyl ester of L-tyrosine and 8.5 g (61.5 mmol) of potassium carbonate are placed in a 250-mL three-necked flask. The solids are dissolved in a mixture of 50 mL acetone and 50 mL water, and the resulting solution is cooled to 5° C. on a water/ice bath. 6.0 mL (62.8 mmol) of ethyl chloroformate is added, in 30 minutes, and then the solution obtained is stirred at room temperature over night. The mixture obtained is transferred to a decanting funnel and the upper phase, of a yellowish colour, is separated. The aqueous phase is washed with 20 mL of ethyl acetate. This organic phase is combined with the preceding, and they are dried and evaporated to dryness. An oil is obtained that weighs 13.6 g (98.3% yield), which is used directly in the next stage.

A 250-mL three-necked flask, equipped with a mechanical stirrer, is loaded with 13.6 g (50.8 mmol) of the oil obtained in the preceding stage, 12.8 g (55.9 mmol) of 2-(5-ethylpyridin-2-yl)ethyl methanesulphonate, obtained by evaporation of the solution in toluene resulting from the first stage of example 1.B, and 8.4 g (61.0 mmol) of potassium carbonate. The mixture is dissolved in 140 mL of isopropyl acetate, and is heated under reflux for 16 hours. At the end of this time, the organic phase is extracted with 2×60 mL of water (adjusting the pH of the aqueous phase to 6). The organic phase is dried and evaporated to dryness. A reddish oil weighing 23.5 g is obtained. NMR analysis of the raw product obtained shows that the proportion of substitution product is lower than that obtained with other protecting groups, yet leaving quite a lot of methanesulphonate unreacted. In view of this result, it was decided to reject the use of this protecting group.

Table I gives a summary of the various protecting groups tested and the overall yield of the stages involved from the methyl ester of tyrosine to compound (IV), according to the following scheme:

| Protecting group Q | Overall yield (%) |
|---|---|
| tert-Butyloxycarbonylamino (Comparative example 1) | 24.1 |
| Benzyloxycarbonylamino (Comparative example 2) | 20.7 |
| Acetylamino (Comparative example 3) | 11.5 |
| Ethyloxycarbonylamino (Comparative example 4) | not isolated |
| Benzylideneamino (Example 1) | 62.8 |

It can be seen, on the basis of the results obtained, that the protecting groups tested in the comparative examples lead to production of the novel compound (IV) at very low yields, in comparison with the yield obtained (62.8%) using the protecting group that is the object of the invention according to example 1, section B.

The invention claimed is:

1. The compound of formula (IV):

[Structure IV: 5-ethyl-2-pyridyl-CH2CH2-O-C6H4-CH2-CH(NH2)-CO2H, with * at chiral center]

or a salt thereof.

2. A method of production of the compound of claim 1, characterized in that it comprises reaction of a compound of formula (VII)

[Structure VII: HO-C6H4-CH2-CH(N=CR1R2)-CO2R]

in which: R can be hydrogen or a $C_1$-$C_4$ alkyl group; each of $R^1$ and $R^2$ is selected individually from hydrogen or an aryl group of formula

[Aryl structure with $R^3$, $R^4$ substituents]

in which $R^3$ and $R^4$ can be, without distinction, hydrogen, or a $C_1$-$C_6$ alkyl group, or a $C_1$-$C_4$ alkoxy group;
with the condition that $R^1$ and $R^2$ cannot both be hydrogen,
with a compound of formula (III)

[Structure III: 5-ethyl-2-pyridyl-CH2CH2-Z]

in which Z is a leaving group, to obtain the compound of formula (VIII)

[Structure VIII: 5-ethyl-2-pyridyl-CH2CH2-O-C6H4-CH2-CH(N=CR1R2)-CO2R]

which, subsequently, is submitted to deprotection of the amino group and when R is a C1-C4 alkyl group hydrolysis of the COOR group of a compound of formula VIII to convert R as alkyl to R as hydrogen.

3. A method according to claim 2, characterized in that R is the methyl group.

4. A method according to claim 2, characterized in that Z is a suiphonic ester.

5. A method according to claim 2, characterized in that Z is the methanesulphonyl (mesyl) group.

6. A method according to claim 2 characterized in that $R^1$ is hydrogen and $R^2$ is an aryl group of formula

[Aryl structure with $R^3$, $R^4$ substituents]

in which $R^3$ and $R^4$ can be, without distinction, hydrogen, a $C_1$-$C_6$ alkyl group or a $C_1$-$C_4$ alkoxy group.

7. A method according to claim 2, characterized in that $R^1$ is hydrogen and $R^2$ is phenyl.

8. A method according to claim 2, characterized in that it comprises reaction of the compound of formula

[Structure: 5-ethyl-2-pyridyl-CH2CH2-OMs]

with the compound of formula

[Structure: HO-C6H4-CH2-CH(N=CHPh)-CO2Me]

to obtain the compound of formula

[Structure: 5-ethyl-2-pyridyl-CH2CH2-O-C6H4-CH2-CH(N=CHPh)-CO2Me]

which, subsequently, is submitted to deprotection of the benzylideneamino group and hydrolysis of the methyl ester.

9. A method for production of pioglitazone which comprises subjecting a compound of formula IV obtained by the process of claim 2, to the following stages:
(a) bromination of compound (IV) to obtain the compound of formula (XI)

[Structure XI: 5-ethyl-2-pyridyl-CH2CH2-O-C6H4-CH2-CH(Br)-CO2H]

(b) condensation of compound (XI) with thiourea to obtain the compound of formula (XII)

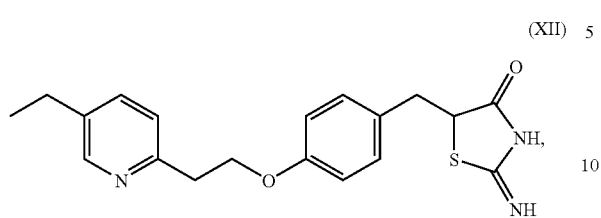
(XII)

(c) hydrolysis of compound (XII) to obtain pioglitazone.

10. A method for production of pioglitazone which comprises subjecting a compound of formula IV to the following steps:

(a) bromination of compound (IV)

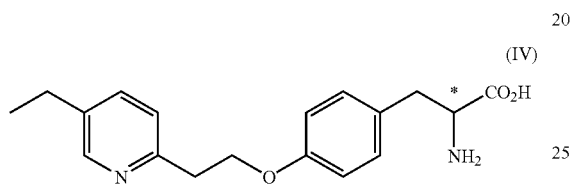
(IV)

to obtain the compound of formula (XI)

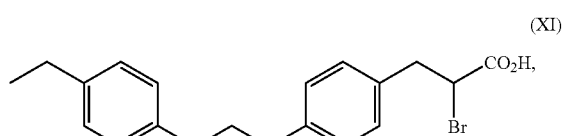
(XI)

(b) condensation of compound (XI) with thiourea to obtain the compound of formula (XII)

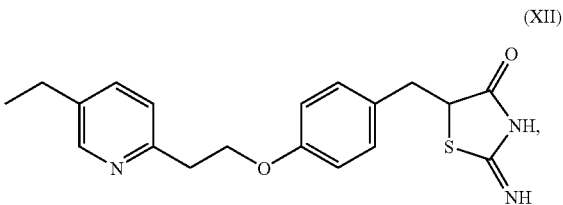
(XII)

(c) hydrolysis of compound (XII) to obtain pioglitazone.

* * * * *